United States Patent [19]

Bezwada et al.

[11] Patent Number: 5,047,048
[45] Date of Patent: Sep. 10, 1991

[54] CRYSTALLINE COPOLYMERS OF P-DIOXANONE AND ε-CAPROLACTONE

[75] Inventors: Rao S. Bezwada, Whitehouse Station; Shalaby W. Shalaby, Lebanon; Mo Erneta, Princeton Junction, all of N.J.

[73] Assignee: Ethicon, Inc., Somerville, N.J.

[21] Appl. No.: 472,134

[22] Filed: Jan. 30, 1990

[51] Int. Cl.$^5$ .................. A61B 17/00; C08G 63/00
[52] U.S. Cl. .................. 606/231; 606/230; 525/411; 525/415; 528/354
[58] Field of Search ......... 606/230, 231; 525/411, 525/415; 528/354

[56] References Cited

U.S. PATENT DOCUMENTS

| | | | |
|---|---|---|---|
| 4,027,676 | 6/1977 | Mattei | 606/230 |
| 4,052,988 | 10/1977 | Doddi et al. | 606/230 |
| 4,605,730 | 8/1986 | Shalaby et al. | 606/231 |
| 4,624,256 | 11/1986 | Messier et al. | 606/231 |
| 4,700,704 | 10/1987 | Jamiolkowski et al. | 606/230 |
| 4,788,979 | 12/1988 | Jarrett et al. | 606/230 |
| 4,791,929 | 12/1988 | Jarrett et al. | 606/230 |

*Primary Examiner*—Stephen C. Pellegrino
*Assistant Examiner*—Gary Jackson
*Attorney, Agent, or Firm*—Matthew S. Goodwin

[57] ABSTRACT

Crystalline copolymers of ε-caprolactone and a monomer having the formula:

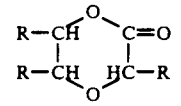

Surgical filaments, especially monofilament sutures, prepared by melt spinning the crystalline copolymers described above.

14 Claims, No Drawings

CRYSTALLINE COPOLYMERS OF P-DIOXANONE AND ε-CAPROLACTONE

BACKGROUND OF THE INVENTION

This invention relates to copolymers derived from p-dioxanone and its homologs, and especially to such crystalline copolymers which can be readily melt spun to prepare fibers suitable for use as absorbable surgical sutures.

U.S. Pat. No. 4,052,988 (Doddi) discloses the preparation of a p-dioxanone homopolymer and its use as an absorbable surgical suture. This synthetic suture exhibits outstanding mechanical and biological properties which make it a viable candidate to replace natural sutures such as surgical gut and collagen for numerous applications.

One of the significant hurdles to overcome before surgeons readily accept a synthetic suture over natural sutures is the stiffness of synthetics. As an example, a well known synthetic suture, which can be prepared from a glycolide homopolymer or a copolymer of lactide and glycolide, is typically braided or twisted to prepare a multifilament suture so that the suture has the requisite flexibilty and handling characteristics. One of the goals of the polymer chemist attempting to synthesize polymers suitable for use as absorbable surgical sutures is to prepare a monofilament suture which has handling properties and flexibility comparable to such properties of multifilament, braided sutures commonly used in the art without sacrificing physical properties.

Although the p-dioxanone homopolymer described in the Doddi Patent goes a long way in reaching the goal toward the preparation of an absorbable monofilament suture with handling properties and flexibilty as good as a braided multifilament, it would be desirable to develop a polymer composition which has even better flexibility relative to a p-dioxanone homopolymer without sacrificing physical properties.

SUMMARY OF THE INVENTION

In one aspect, the invention is a crystalline copolymer of a monomer represented by the formula:

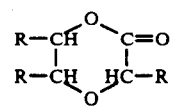

wherein each R is independently hydrogen or methyl; and an amount of ε-caprolactone effective to lower the modulus of the copolymer relative to the modulus of a p-dioxanone homopolymer.

In another aspect, the invention is an absorbable surgical filament prepared by melt spinning the crystalline copolymer described above.

The crystalline copolymers of this invention can be readily melt spun using conventional techniques to prepare fibers having the combination of physical and biological properties necessary for use as an absorbable monofilament surgical suture. Monofilaments prepared from the crystalline copolymers have a lower Young's Modulus relative to the Young's Modulus of a monofilament prepared from a p-dioxanone homopolymer. A reduction in the Young's Modulus correlates to a more flexible and pliable filament, and therefore the handling characteristics of the suture are enhanced.

In preferred embodiments, especially when monofilaments are prepared from block copolymers of this invention, the straight tensile strength and knot tensile strength are substantially equivalent to these properties of a monofilament prepared from a p-dioxanone homopolymer. Lastly, the in vivo absorption profile of sutures prepared from the block copolymers of this invention is comparable to the profile of sutures prepared from a p-dioxanone homopolymer. This is surprising since homopolymers of ε-caprolactone are substantially nonabsorbable for periods up to one year.

The crystalline copolymers are useful for the preparation of absorbable surgical filaments, especially absorbable monofilament surgical sutures, although these copolymers may find use in the preparation of other surgical devices. For example, the copolymers may be used for the preparation of surgical meshes, surgical staples, hemostatic clips, and the like.

DETAILED DESCRIPTION OF THE INVENTION

The crystalline copolymers of this invention are prepared from ε-caprolactone and a predominant amount of a monomer having the formula:

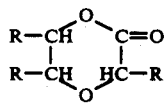

wherein each R is independently hydrogen or methyl. Preferably, each R is hydrogen and the monomer is 1,4-dioxan-2-one, which is commonly referred to as p-dioxanone. For ease of discussion, the monomer represented by the formula above will be referred to as the p-dioxanone monomer or simply, p-dioxanone, but this language is intended to encompass all monomers embodied in this formula. A predominant amount of the p-dioxanone monomer generally refers to an amount of monomer greater than 50 weight percent of the comonomer composition from which the crystalline copolymer of this invention is derived.

In a preferred embodiment, the crystalline copolymers have a degree of crystallinity and an intrinsic viscosity which render the copolymers suitable for extrusion into fibers or films and for injection molding into surgical devices such as staples. Advantageously, the crystallinity of the copolymers is greater than about 10 percent as measured by x-ray diffraction, so that the copolymer can maintain its structural integrity at the elevated temperatures required for extrusion and molding. Preferably, the intrinsic viscosity of the crystalline copolymers ranges from about 0.8 to about 3.5, more preferably from about 1.2 to about 3.0 dl/g in a 0.1 g/dl solution of hexafluoroisopropyl alcohol (HFIP) at 25° C. A copolymer with an intrinsic viscosity below about 0.8 dl/g generally lacks sufficient viscosity to provide suitable melt strength for extrusion or molding, and a copolymer with an intrinsic viscosity above about 3.5 dl/g is generally too viscous for melt processing.

The copolymers of this invention can be random or block copolymers. For the preparation of random copolymers, the amount of ε-caprolactone in the monomer composition from which the random copolymer is prepared is desirably within the range of about 2 to about 20 weight percent. Amounts below about 2 percent generally will not have the effect of reducing the modulus of the copolymer, and amounts greater than 20 percent may compromise the physical properties of the copolymer, to the extent that the copolymer may no longer be suitable for use as an absorbable surgical suture. A more preferred range is between about 2 to about 10 percent, with the most preferred range being between about 2 and about 5 percent.

For the preparation of block copolymers, the concentration range for ε-caprolactone in the monomer composition from which the block copolymer is prepared is desirably between about 5 to about 40 weight percent. An amount below about 5 percent generally fails to reduce modulus and amounts greater than about 40 percent may compromise physical properties, e.g straight or knot tensile strength. A preferred range is between about 5 to about 30 weight percent, and the most preferred range is between about 5 to about 20 percent.

The random copolymers of this invention can be prepared by polymerizing the desired proportions of p-dioxanone and ε-caprolactone in the presence of an organometallic catalyst and an initiator at elevated temperatures. The organometallic catalyst is preferably a tin-based catalyst, e.g. stannous octoate, and is present in the monomer mixture at a mole ratio of monomer to catalyst ranging from 15,000 to 40,000/1. The initiator is typically an alkanol, a glycol, a hydroxyacid, or an amine, and is present in the monomer mixture at a mole ratio of monomer to initiator ranging from 750 to 2000/1. The polymerization is typically carried out at a temperature range from 80° to 160° C., preferably 80°-140° C., until the desired molecular weight and viscosity are achieved.

The preferred copolymers of this invention are block copolymers of the p-dioxanone monomer and ε-caprolactone. Unlike the random copolymers, the block copolymers are semi-crystalline and have mechanical properties substantially equivalent to the mechanical properties of a p-dioxanone homopolymer. The block copolymers can be characterized as having the following repeating blocks:

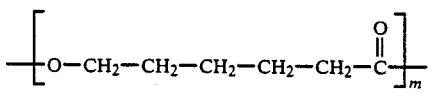

polycaprolactone
("A" block)

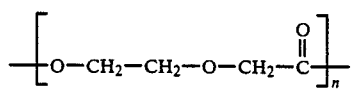

polydioxanone
("B" block)

wherein m and n are each a number greater than 1.

The block copolymers can be prepared as diblock copolymers (—AB—) or triblock copolymers (—BAB—). Diblock copolymers can be prepared by first prepolymerizing ε-caprolactone with a monofunctional initiator such as an alkanol or an amine, and then polymerizing p-dioxanone with the prepolymer using standard techniques known in the art. The polymerization conditions and ratio of constituents described above for the preparation of random copolymers can be used for preparing the prepolymer and the diblock copolymer, except that the prepolymerization is generally carried out at higher temperatures, e.g 160°-190° C., for a maximum of 24 hours. Triblock copolymers are prepared in a similar manner, except that the initiator used for prepolymerization of the ε-caprolactone is a difunctional initiator such as a glycol.

Once the desired random or block copolymer is prepared, absorbable filaments exhibiting the requisite properties for use as surgical sutures may be prepared using conventionally accepted methods well known in the art by first melt extruding the copolymer through a spinnerette to prepare fibers, drawing the fibers to create orientation, and then annealing the oriented fibers to enhance dimensional stability. Additionally, the sutures can be attached, if desired, to one or more needles. See, for example, U.S. Pat. Nos. 4,653,497 and 4,838,267, which also describe in detail the testing procedures used for determining the physical and biological properties of those monofilaments described in the examples of this specification.

In preferred embodiments of this invention, absorbable surgical monofilaments prepared from copolymers of p-dioxanone and ε-caprolactone have a straight tensile strength of at least 50,000 psi, preferably 60,000 psi, and a knot tensile strength of at least 30,000 psi, preferably 40,000 psi. The Young's Modulus for preferred embodiments is typically below 400,000 psi, preferably 300,000 psi, and more preferably below 100,000. The percent elongation is typically less than 80 percent, preferably less than 40 percent, and more preferably less than 30 percent.

The in vivo absorption profile of a surgical filament implanted in the tissue of an animal is often a critical factor in determining the desirability of one synthetic suture over another. Surprisingly, the surgical filaments prepared from block copolymers of this invention in preferred embodiments exhibit an in vivo absorption profile comparable to that of filaments prepared from a p-dioxanone homopolymer. Complete absorption of the surgical filaments of this invention implanted in tissue will generally occur not more than 210 days after implantation, while filaments prepared from a polycaprolactone homopolymer show no sign of absorption after this period of time.

The following examples are intended to illustrate but in no way limit the scope of the claimed invention. As the terms are used in the examples, PCL and PDO refer to polymers of ε-caprolactone and 1,4-dioxan-2-one.

EXAMPLE 1

DIBLOCK COPOLYMER OF PCL/PDO AT 8.9/91.1 BY WT

A flame dried, 250 ml round bottom single neck flask is charged with 10 grams (8.9 wt. percent) of monohydroxy-terminated polycaprolactone prepolymer with a weight average molecular weight of 10,000 as determined by gel permeation chromatography (GPC) supplied by Scientific Polymer Products Inc. The reaction flask is held under high vacuum at 80° C. for about 64 hours. After cooling to room temperature, the reaction flask is charged with 102.1 gm (1.0 mole, 91.1 wt. percent) of 1,4-dioxan-2-one, and 0.101 ml of stannous octoate (0.33 molar solution in toluene). The contents of the reaction flask are held under high vacuum at room temperature for about 16 hours. The flask is fitted with a flame dried mechanical stirrer and an adapter. The reactor is purged with nitrogen three times before being vented with nitrogen. The reaction mixture is heated to 90° C., and maintained at this temperature for about 75 minutes. The temperature of the reaction mixture is raised to 110° C. and maintained at this temperature for about 4 hours, lowered to 90° C. and maintained at this temperature for 24 hours, and then lowered to 80° C. and maintained at 80° C. for three days. The copolymer is isolated and dried for 8 hrs at 60° C., and for 8 hrs at 70° C. under high vacuum (0.1 mmHg) to remove any unreacted monomer (about 15 percent). The copolymer has an inherent viscosity of 2.18 dl/g in hexafluoroisopropyl alcohol (HFIP) at 25° C., and a melting point range by hot stage microscopy between 108°-112° C.

The copolymer is melt spun, drawn and annealed to prepare oriented, dimensionally stable filaments using conventional extrusion techniques. The mechanical and biological properties of these filaments are reported in Table 1, which also includes these properties for a p-dioxanone homopolymer for comparison

TABLE 1

Mechanical and Biological Properties of PCL/PDO Diblock Copolymer

| Example No. | 1 | Control[1] |
|---|---|---|
| Fiber Properties | Annealed | |
| | (6 hrs./80° C./5% relax.) | |
| Diameter (mils) | 7.96 | 6.6 |
| Str. Tensile, PSI | 80,023 | 74,000 |
| Knot Tensile, PSI | 49,759 | 55,000 |
| Elongation, percent | 40 | 29 |
| Young's Modulus, PSI | 199,836 | 324,000 |
| In Vitro BSR[2] | | |
| % BSR, | | |
| 4 days | 84 | 84 |
| 7 days | 77 | 78 |
| In Vivo Absorption[3] | | |
| Days after Implantation | | |
| 5 | 100 | — |
| 91 | 89 | — |
| 119 | 83 | — |
| 154 | 36 | — |
| 210 | 0 | — |

[1]PDS ™ violet monofilament polydioxanone suture
[2]Breaking Strength Retention (BSR) in vitro is the percent of original straight tensile strength remaining after the indicated number of days in phosphate buffer, pH = 7.27 at 50° C.
[3]Median percent of original cross sectional area remaining after intramuscular implantation in rats for the indicated number of days, determined according to the procedures described in U.S. Pat. No. 4,653,497

The data from Table 1 shows that a surgical filament prepared from a block copolymer of ε-caprolactone and p-dioxanone has equivalent straight and knot tensile strength relative to such properties for filaments prepared from a p-dioxanone homopolymer, but has significantly enhanced flexibility as demonstrated by the reduction in Young's Modulus relative to the filaments prepared from the p-dioxanone homopolymer. Additionally, complete absorption in vivo occurred within 210 days, which is comparable to the rate of absorption for a p-dioxanone homopolymer.

EXAMPLE 2

TRIBLOCK COPOLYMER OF PCL/PDO AT 10/90 BY WT

A flame dried, 250 ml, round bottom single neck flask is charged with 54.0 g (0.4731 mole) distilled ε-caprolactone, 0.0225 ml (0.5 mmole/mole of total monomer) distilled diethylene glycol, and 0.0574 ml stannous octoate (0.33 molar in toluene). The contents of the reaction flask are held under high vacuum at room temperature for about 4 hours. The flask is fitted with a flame dried mechanical stirrer and an adapter. The reactor is purged with nitrogen before being vented with nitrogen. The reaction mixture is heated to 190° C. and maintained there for 16 hours. The resulting dihydroxy-terminated polycaprolactone prepolymer is isolated and dried for about 24 hours at 50° C./0.1 mmHg to remove any unreacted monomer. It has an inherent visocity of 1.75 dl/g in HFIP and the free monomer is less than 0.1% by NMR.

Five grams of the dihydroxy-terminated polycaprolactone prepolymer is charged into a flame dried, 100 ml round botton, single neck flask. The contents of the reaction flask are held under high vacuum at 50° C. for about 16 hours. After cooling to room temperature, the reaction flask is charged with 45 gms (0.4408 mole) of 1,4-dioxan-2-one, and 0.0445 ml of stannous octoate (0.33 molar solution in toluene). The reaction flask is fitted with a flame dried mechanical stirrer and an adapter. The reactor is purged with nitrogen three times before being vented with nitrogen. The reacton mixture is heated to 110° C. and maintained there for about 8 hours. The copolymer is isolated and dried for about 64 hours at 70° C./0.1 mmHg and for about 32 hours at 80° C./0.1 mmHg to remove any unreacted monomer. The copolymer conversion is 79%, and the copolymer has an inherent viscosity of 2.47dl/g, and a melting point of 104° C.

EXAMPLE 3

TRIBLOCK COPOLYMER OF PCL/PDO AT 20/80 BY WT.

The procedure of Example 2 is substantially repeated, except that 10 gms of the polycaprolactone prepolymer are reacted with 40 gms (0.3918 mole) of 1,4-dioxan-2-one, and 0.0396 ml of stannous octoate (0.33 molar solution in toluene). The copolymer conversion is 85%, and the copolymer has an inherent visocity of 1.82 dl/g and a melting point of 105°-106° C.

EXAMPLE 4

RANDOM COPOLYMER OF PCL/PDO AT 90/10 BY WT.

A flame dried 250 ml, round bottom single neck flask is charged with 90 gms (0.7885 mole) of distilled ε-caprolactone, 10 gms (0.0980 mole) of 1,4-dioxan-2-one, 0.0253 ml of distilled diethylene glycol, and 0.108 ml of stannous octoate (0.33 molar solution in toluene). The contents of the reaction flask are held under high vacuum (0.1 mmHg) for about 16 hours. The flask is fitted with a flame dried mechanical stirrer and an adapter. The reactor is purged with nitrogen three times before being vented with nitrogen. The reaction mixture is heated to 160° C. and maintained at this temperature for about 24 hours, and then cooled to 110° C. and maintained at this temperature for an additional 24 hours. The copolymer is isolated and devolatilized at 50° C./16 hours/0.1 mmHg and at 80° C./48 hrs/0.1 mmHg. The copolymer conversion is 99.5%, and the copolymer has an inherent visocity of 3.09 dl/g and a melting point 48°-50° C.

Each of the copolymers from Examples 2-4 are melt spun, drawn and annealed to prepare oriented, dimensionally stable filaments using conventional extrusion techniques. The mechanical properties of these filaments are reported in Table 2, which also includes the mechanical properties of a homopolymer of 1,4-dioxan-2-one for comparison.

TABLE 2

MECHANICAL PROPERTIES OF PCL/PDO COPOLYMERS

| Example No. | 2 | 3 | 4 | Control[1] |
|---|---|---|---|---|
| Polymer Composition | PCL/PDO at 10/90 (Triblock Copolymer) | PCL/PDO at 20/80 (Triblock Copolymer) | PCL/PDO at 90/10 (Random Copolymer) | |
| Intrinsic Viscosity, dl/g | 2.47 | 1.82 | 3.09 | 1.88 |
| Melting Point | 104 | 105–106 | 48–50 | 109° C. |
| Percent Conversion | 79 | 85 | 99.5 | 95 |
| Fiber Properties (Ann. 12 hrs/60° C./0% relax.) | | | | |
| Diameter (mils) | 7.8 | 7.8 | 7.1 | 6.6 |
| Straight Tensile Strength, Kpsi | 90 | 73 | 76 | 74 |
| Knot Tensile Strength, Kpsi | 56 | 55 | 38 | 55 |
| Percent Elongation | 35 | 32 | 21 | 29 |
| Young's Modulus, Kpsi | 271 | 298 | 127 | 324 |

[1]PDS ™ violet monofilament polydioxanone suture

The data from Table 2 shows a reduction in Young's Modulus for filaments prepared from copolymers of this invention relative to filaments prepared from a p-dioxanone homopolymer. It is also noteworthy to point out that the block copolymers retain their knot tensile strength relative to a typical knot tensile strength reported for a p-dioxanone homopolymer.

EXAMPLE 5

RANDOM COPOLYMER OF PCL/PDO AT 95/5 BY MOLE

A thoroughly dried mechanically stirred 5-gallon stainless steel reactor is charged under nitrogen purge with 13.67 kg (133.90 moles) of 1,4-dioxan-2-one, 804.80 gm (7.05 mole) of ε-caprolactone, 14.5 gms of D&C Violet #2 violet dye, 26.3 gms of 1-dodecanol, and 22.7 ml of stannous octoate (0.33 molar in toluene). The contents of the reactor are held under vacuum for a few minutes, then the reactor is purged with nitrogen. The reaction mixture is heated to 115° C. and maintained there for 6 hours, and then oven cured at 80° C. for 115 hours. The polymer is isolated, ground, sieved, and then dried under vacuum in a tumble drier at 70° C./42 hours to remove unreacted monomer. Polymer and fiber properties are summarized in Table 3.

EXAMPLE 6

PREPARATION OF RANDOM COPOLYMER OF PCL/PDO AT 92.5/7.5 BY MOLE

The copolymer is prepared using a procedure similar to that of Example 1, except the following changes are made:

| | |
|---|---|
| 1,4-dioxan-2-one | 12.094 Kg (118.47 mole) |
| ε-Caprolactone | 1.096 Kg (9.60 mole) |
| 1-dodecanol | 23.86 gm. |
| Sn(Oct)₂ (0.33 molar solution in toluene) | 20.59 ml |
| Reaction Time | 8 hours/125° C. |
| | 144 hours/80° C. |

Polymer and fiber properties are summarized in Table 3.

TABLE 3

| | EXAMPLE 5 | EXAMPLE 6 | CONTROL[1] |
|---|---|---|---|
| Copolymer Properties | | | |
| Intrinsic Viscosity, dl/g | 1.85 | 1.56 | 1.88 |
| Final Comp. by NMR | 94.6/5.4 | 92.9/7.9 | 100/0 |
| PDO/PCL, Mole % | | | |
| Melting Temperature (hot stage Microscropy) | 94.5° C. | 91° C. | 109° C. |
| Fiber Properties (Annealed 12 hrs/60° C.) | | | |
| Diameter (mils) | 8.2 | 7.8 | 6.6 |
| Str. Tensile, Kpsi | 79 | 60 | 74 |
| Knot Strength, Kpsi | 51 | 42 | 55 |
| Elong. at Break | 31% | 28% | 29 |
| Young's Modulus, Kpsi | 213 | 162 | 324 |
| In Vivo BSR[2], Percent 21 days | 44 | — | 70 |

[1]PDS ™ violet monofilament polydioxanone suture
[2]BSR in vivo is the median percent of original breaking strength remaining after implantation in the dorsal subcutis of rats for the indicated number of days.

The data from Table 3 shows a significant reduction in Young's Modulus for random copolymers of this invention relative to that of a p-dioxanone homopolymer. Although the examples only show the properties for copolymers of p-dioxanone and ε-caprolactone in specific proportions, similar outstanding results may be obtained for copolymers derived from p-dioxanone homologs and for copolymers with varying proportions of ε-caprolactone. Such copolymers have been described in this specification and are within the scope of the claimed invention.

What is claimed is:

1. A crystalline copolymer of a monomer represented by the formula:

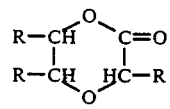

wherein each R is independently hydrogen or methyl; and from about 5 to about 40 weight percent ε-caprolactone.

2. The crystalline copolymer of claim 1 wherein the crystallinity of the copolymer is greater than about 10 percent as measured by x-ray diffraction.

3. The crystalline copolymer of claim 2 wherein the intrinsic viscosity of the copolymer ranges from about 1.2 to about 3.0 dl/g.

4. The crystalline copolymer of claim 3 wherein the copolymer is a block copolymer.

5. The crystalline copolymer of claim 4 wherein the monomer represented by the formula is 1,4-dioxan-2-one.

6. The crystalline copolymer of claim 5 wherein the amount of ε-caprolactone ranges from about 5 to about 30 weight percent.

7. The crystalline copolymer of claim 6 wherein the amount of ε-caprolactone ranges from about 10 to about 20 weight percent.

8. An absorbable surgical filament prepared by melt spinning the copolymer of claim 1 or 7.

9. The absorbable surgical filament of claim 8 wherein the Young's Modulus is not greater than 300,000 psi.

10. The absorbable surgical filament of claim 9 wherein complete in vivo absorption of the filament implanted in an animal is not more than 210 days after implantation.

11. The absorbable surgical filament of claim 10 wherein the straight tensile strength is at least 50,000 psi and the knot tensile strength is at least 30,000 psi.

12. The absorbable surgical filament of claim 11 wherein the percent elongation is not greater than 80 percent.

13. The absorbable surgical filament of claim 12 in the form of a monofilament.

14. The absorbable surgical filament of claim 13 in the form of a suture with or without a needle.

* * * * *